(12) United States Patent
Smith et al.

(10) Patent No.: US 6,248,083 B1
(45) Date of Patent: Jun. 19, 2001

(54) DEVICE FOR PRESSURE MEASUREMENTS

(75) Inventors: Leif Smith; Lars Tenerz, both of Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

(21) Appl. No.: 09/399,097

(22) Filed: Sep. 20, 1999

Related U.S. Application Data

(60) Provisional application No. PCT/SE98/00541, filed on Mar. 25, 1998, and provisional application No. 60/042,387, filed on Mar. 25, 1997.

(51) Int. Cl.[7] ................................................. A61B 5/00
(52) U.S. Cl. ............................................ 600/585; 600/561
(58) Field of Search ................................... 600/434–436, 600/585, 549, 561

(56) References Cited

U.S. PATENT DOCUMENTS

| | | | |
|---|---|---|---|
| 4,301,677 | 11/1981 | Fisher | 73/105 |
| 4,734,873 | 3/1988 | Malloy et al. | 364/571 |
| 5,551,301 | 9/1996 | Cowan | 73/708 |

FOREIGN PATENT DOCUMENTS

| | | |
|---|---|---|
| 0 712 603 | 5/1996 | (EP) . |
| 91/05575 | 5/1991 | (WO) . |
| 96/07351 | 3/1996 | (WO) . |
| 97/29678 | 8/1997 | (WO) . |
| 99/40856 | 8/1999 | (WO) . |

OTHER PUBLICATIONS

Cardiometrics WaveWire™ Pressure Guide Wire Apr. 6, 1998 Rev. C.

*Primary Examiner*—Max Hindenburg
(74) *Attorney, Agent, or Firm*—Foley & Lardner

(57) ABSTRACT

The invention relates to a guide wire assembly, having a guide wire (2) having a distal end portion (16) and a proximal end, wherein a measuring device (14) is mounted in the distal end portion (16) of the guide wire (2). It also has an interface cable (4) having a first end connectable to a control unit (8), and a second end connectable to the proximal end of the guide wire. Furthermore there is provided information storage (20; 22; $R_x$) on the interface cable, containing calibration/temperature compensation data, uniquely characteristic of the measuring device. The data and an uncompensated output from the measuring device forming the input for calculation of a correct measurement value.

21 Claims, 4 Drawing Sheets

DEVICE FOR PRESSURE MEASUREMENTS

The Applicants hereby claim the benefit of PCT application PCT/SE98/00541, filed Mar. 25, 1998 (and which designated the United States and was published as WO 98/42253), and U.S. Provisional Application 60/042,387, filed Mar. 25, 1997. the entire contents of this PCT application and U.S. Provisional application are incorporated herein by reference.

The present invention relates to a device for in situ pressure measurements, especially intracoronary pressure, said device comprising a guide wire having a pressure sensor provided at its distal end. In particular the invention relates to a such a device having a disconnectable guide wire, wherein there is provided temperature compensation circuitry external of said guide wire.

BACKGROUND OF THE INVENTION

Most conventional piezoresistive pressure sensors employ the full bridge principle, i.e. an entire Wheatstone bridge, comprising four resistors, is located on a membrane. There are certain advantages with such a solution, and some disadvantages. The advantages are that they have a high sensitivity, little temperature sensitivity, and a low off set.

The major disadvantage is that they are bulky and thus impose a lower limit on the dimensions of the sensor.

Another major problem associated with all pressure sensors, and in particular with ultraminiature pressure sensors, is to manage to manufacture identical elements in all batches over time. It is virtually inevitable that the sensor characteristics differ from sensor to sensor and hence there will always be a need for some kind of individual calibration of each sensor. Typically it is necessary to calibrate the output signal for a change in temperature, i.e. the pressure response of each sensor will have individual and varying degrees of temperature dependence.

In European patent application 85100922.5 (corresponding to U.S. Pat. No. 4,734,873) there is disclosed to store the sensor characteristics in a PROM and to utilize a computer for the calculation of the calibrated signal.

Another alternative used for piezoresistive pressure sensors is to integrate a resistor net on the chip or in the vicinity of the chip, in order to normalize the signals.

Sensors from CAMINO and other pressure sensor devices comprise components that have been individually matched for the sensor element in order to calibrate the sensor device.

U.S. Pat. No. 5,551,301 (Cardiometrics) discloses a method of calibrating a sensor using two amplifiers and a computer.

An important problem associated with the ultraminiature devices comprising additional resistors and/or other components, such as PROMs, provided on the device, is the small dimensions of the sensor. The mentioned components are simply too large to be easily integrated in a sensor element, if the necessary degree of miniaturization is to be achieved. There may also be required too many connection leads between the sensor and the electronic circuitry, which prevents the miniaturization. The higher the number of leads is, the closer to each other the leads have to be placed, and thus the higher the risk for short-circuit and damage on the leads will be.

Another important aspect of employing guide wires, is that it is necessary to be able to disconnect the guide wire from external devices. This is because for e.g. dilatation purposes, after having measured pressure and identified a stricture, it will be necessary to insert a balloon catheter in the coronary vessel. This catheter is inserted by threading it into the guide wire, and using the guide wire to pass the balloon to the desired site of dilatation. Therefore the guide wire and an interface cable must be connectable to and disconnectable from each other in order to allow this insertion of a balloon catheter.

SUMMARY OF THE INVENTION

In view of the above, the object of the invention is to provide devices for pressure measurements having an ultraminiature sensor and calibration/compensation circuitry specific to each individual sensor. This object is achieved with the device described herein.

According to the invention, by separately locating bulky portions of the necessary circuitry, or elements or components of such circuitry that are very difficult to miniaturize, such as storage means for sensor specific calibration data, on an interface cable that is disconnectable from a guide wire carrying the sensor, or by splitting the Wheatstone bridge in two parts, one part located on the sensor chip, the other on said interface cable, several advantages are obtained.

First, the miniaturization of the sensor can be driven further, secondly the manufacture of the calibration and compensation circuitry is much simpler, thirdly each chip may be treated as an individual, and thus variations in the manufacture process will be of minor importance.

BRIEF DESCRIPTION OF THE DRAWINGS

The invention will now be described in detail with reference to the drawings, in which.

PREFERRED EMBODIMENTS AND BEST MODE OF OPERATION

Figure 1:
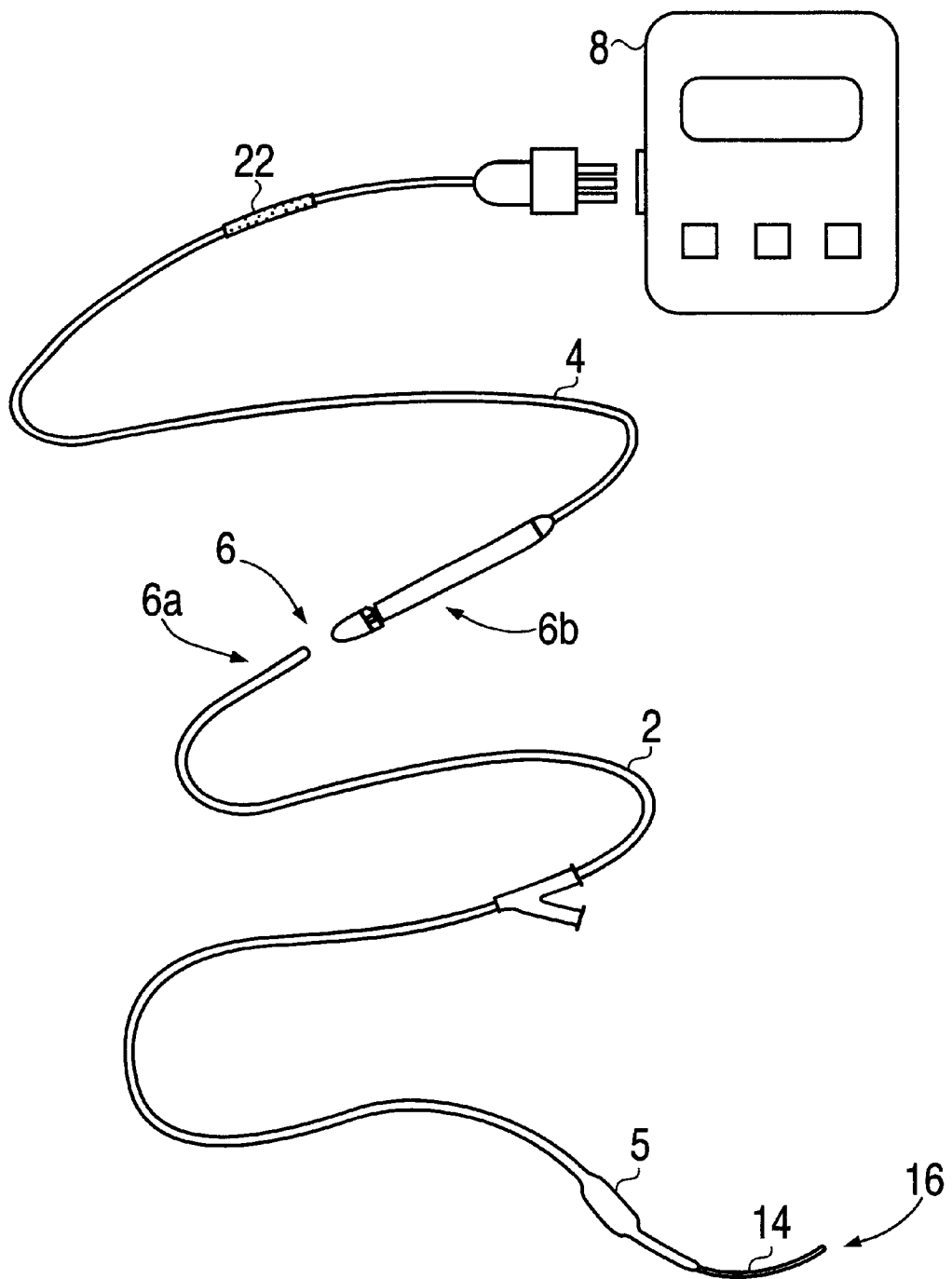
FIG. 1 is an overview of the device including the thin flexible distal part, the cable between the thin distal part and the electronic unit including means for calibration.

An overview of the basic concept and design of the apparatus of the invention is shown schematically in FIG. 1.

Thus, the device for pressure measurements according to the present invention comprises a thin and flexible guide wire 2, suitably having an external diameter of approximately 0.36 mm. An interface cable 4 is also provided. The guide wire and the interface cable are connectable with each other via a suitable connector 6 having mating male 6a and female 6b parts. The male part is provided by the proximal end of the guide wire 2, and the female part is provided on the distal end of the interface cable 4. Suitably, the connector means disclosed in our applications PCT/SE98/00542 (filed Mar. 25, 1997), 09/047,456 (filed Mar. 25, 1998), and 08/927,677 (filed Sep. 10, 1997) are used. The interface cable 4 is connectable to electronic means 8 for signal processing, such as a computer or some other control unit.

Also shown in FIG. 1 is a balloon catheter 5 having been threaded onto the guide wire 2. This is simply achieved by disconnecting the guide wire 2 from the interface cable 4, and passing the balloon catheter 5 onto the guide wire 2, and when the balloon catheter is properly located, the guide wire may be connected again for further measurements. There may also be another catheter (not shown) disposed on the guide wire, which was initially used for locating the guide wire. Such a catheter is normally wide enough that the balloon catheter be inserted inside it, in the space between the guide wire and said catheter.

The guide wire comprises a solid core wire extending along the length thereof, electrical leads being provided on said core wire, under a protective tubing which is provided on the core wire. A pressure sensor 14 is mounted on the core wire, in the distal end 16 portion of the guide wire.

The device of the invention comprises electrical circuitry for calibration and/or temperature compensation purposes (various embodiments thereof to be described in detail below). The electrical circuit means comprises a pressure dependent part provided on said guide wire, and a pressure independent part provided on the proximal side of said connector. The pressure sensitive element on the sensor 14 forms part of said electrical circuit means.

Furthermore there is provided information storing means on said interface cable. This storing means contains calibration and/or temperature compensation data, characteristic of said sensor element.

The information storing means may be an EPROM 20, containing information representing a calibration curve for said pressure sensor, the contents of the EPROM being read out to a control unit, such as a computer, and used in calculation of corrected pressure values.

The information storing means may also be implemented in said electrical circuit as a resistor net, comprising one or more compensation resistors. The resistors are trimmed at manufacture. Thereby the calibration information becomes inherent in the circuit.

It is also conceivable that the information storing means be a bar code 22 provided on a label on said interface cable. The bar code may e.g. represent a 20-digit number, which is sufficient to define a complete calibration curve. In order to make use of said information the user would read the barcode into the computer by conventional means, such as a light pen, and the computer would then be able to add or subtract a correction from the signal received from the measurement and thus to calculate correct pressure.

First Embodiment (Active Calibration)

Figure 2:
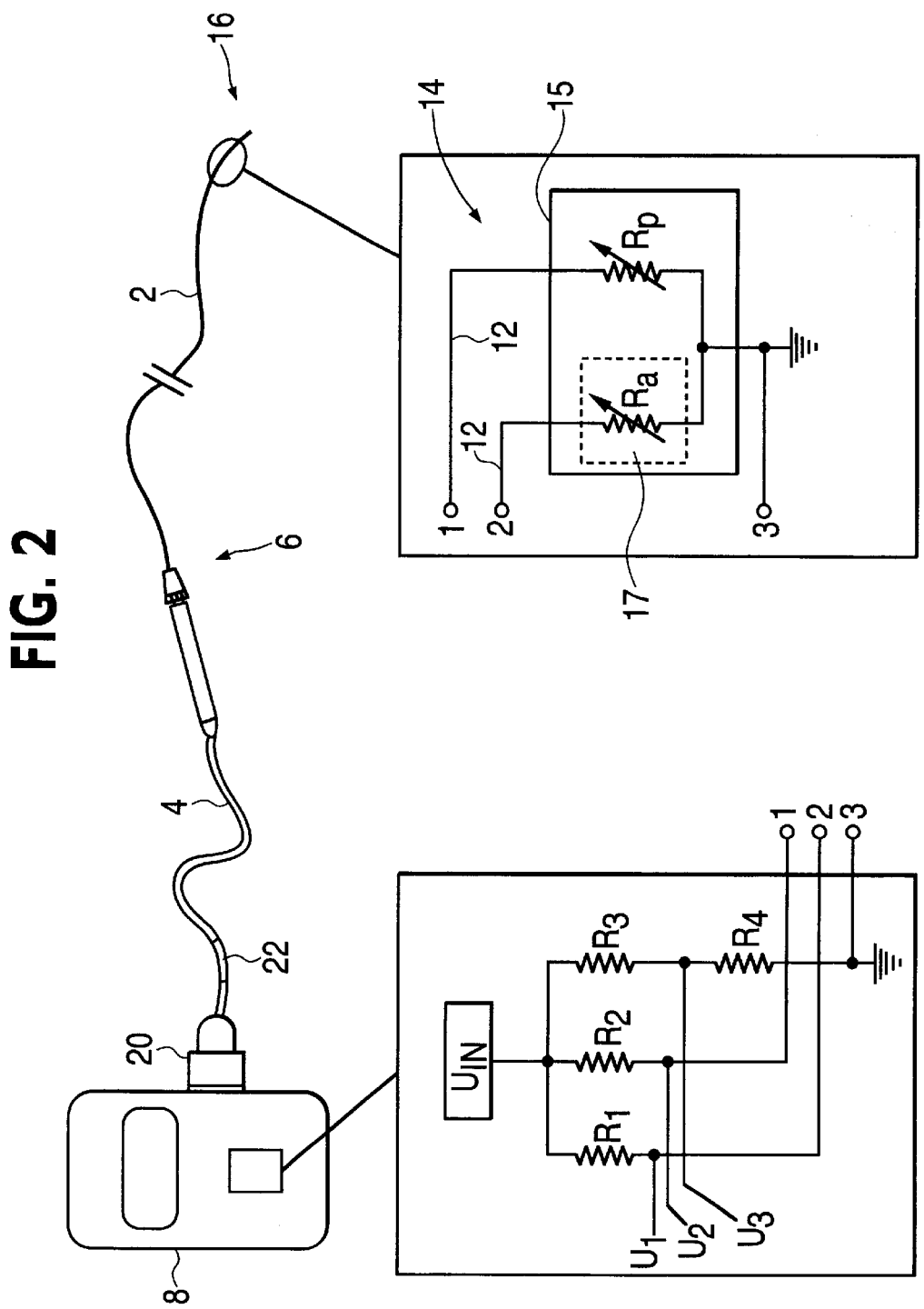
FIG. 2 shows a first embodiment of the invention, comprising separation of a double Wheatstone bridge for the active calibration.

With reference to FIG. 2 a first embodiment of the device according to the invention comprising means for calibrating will now be described. The employed calibration principle is referred to as an "active" temperature calibration. In active calibration, temperature dependence characteristics are determined and stored, for example, in a PROM, and each measurement signal is temperature compensated at the time of measurement.

The electric circuit in this case is a double Wheatstone bridge, wherein the active (pressure sensitive element) piezoresistor $R_a$ is located on the membrane 17 of the sensor 14. The passive (pressure independent element) register $R_p$ is mounted in the vicinity of $R_a$, by preferably on a substrate 15 and not on the membrane. First end of both $R_a$ and $R_p$ is connected to common ground. The remaining resistors $R_{1-4}$ are fixed resistors, and are located external of the sensor, preferably in an external control unit or on the interface cable. A second end of $R_a$ is connected via a suitable lead 12 to a first end of one fixed resistor $R_1$. The second end of $R_1$ is connected to an excitation voltage source. A second end of $R_p$ is connected via a suitable lead 12 to a first end of another fixed resistor $R_2$. The second end of R2 is connected to the same excitation voltage source as R1. Fixed resistors $R_3$ and $R_4$ are connected in series to the common ground. At the other end $R_3$ and $R_4$ are connected to the same excitation voltage as $R_1$ and $R_2$.

There are three voltages $U_1$, $U_2$, $U_3$ (reference ground) of interest in the bridge. $U_1$ exists at a point between R1 and $R_a$. $U_2$ exists at a point between $R_2$ and $R_p$. $U_3$ exists at a point between $R_3$ and $R_4$. The temperature and pressure dependent signal corresponding to $$U(P,T)_{out} = U_1 - U_2.$$

is continuously monitored, as is the difference $$U(T)_{out} = U_2 - U_3$$

which represents the temperature dependent signal.

Figure 3:
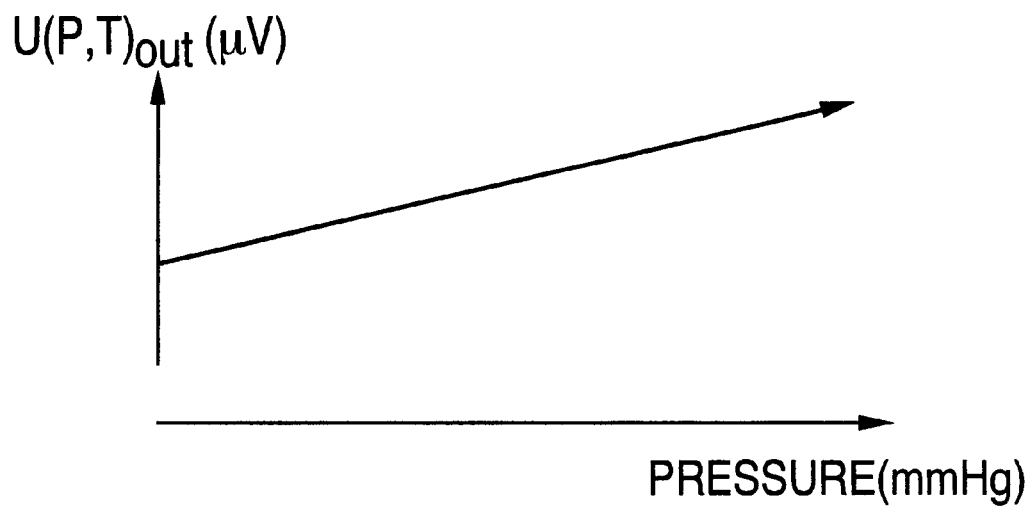
FIG. 3 is a pressure calibration curve at constant temperature.

When the guide wire has been assembled the calibration is performed as follows:

The proximal end is connected to an interface cable via a female connector, and the assembly is connected to the control unit via the proximal contact of the interface cable. The sensor is immersed in a constant temperature water bath inside a pressure chamber. The temperature is normally kept at approximately 37° C., the important thing however being that it be constant. The quantity $U(P,T)_{out} = U_1 - U_2$ is monitored while the pressure is increased, and a plot of $U(P,T)_{out}$ vs P is obtained, an example of which being shown in FIG. 3. The slope $K_{37}$ of this plot represents the sensitivity for the sensor at 37° C., and is stored in said information storing means. This means that the uncompensated pressure value is calculated as $P = U_{out}/K_{37}$, assuming no temperature dependence of the sensitivity.

The sensitivity, $K_{37}$, is itself slightly temperature dependent, and could in principle be determined separately and used for further compensation. However, at present the sensor is calibrated at 37° C., and a minor error at 20° C. is accepted. If said temperature dependence factor is determined separately it may be stored in said storing means together with other calibration data.

Figure 4:
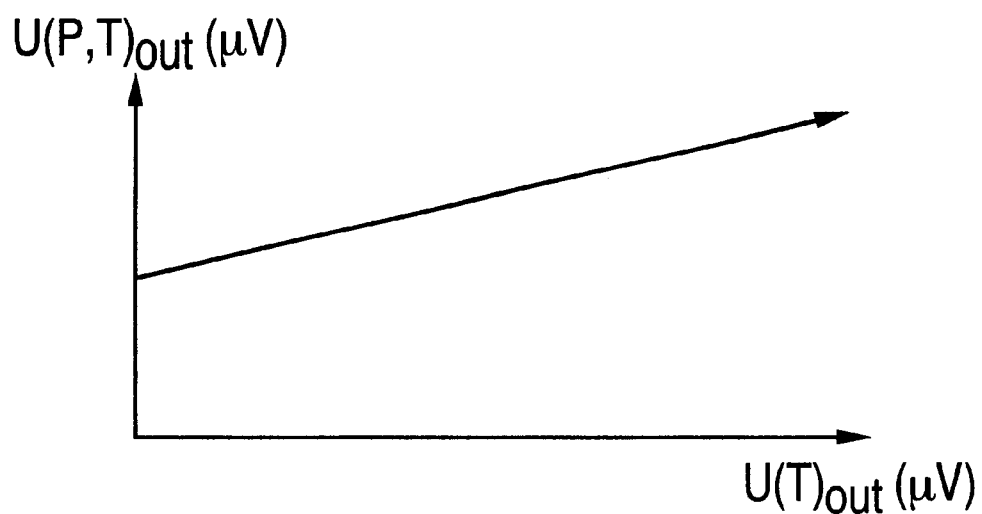
FIG. 4 is temperature off set curve at constant pressure.

Next the so called Temperature Offset (TO) is measured. This is done by immersing the sensor in a water bath at atmospheric pressure and changing the temperature, while monitoring $U(P,T)_{out}$ at the same time $U(T)_{out}$ is monitored and the two quantities are plotted against each other, as shown in FIG. 4.

Thus, a plot of $U(P,T)_{out}$ vs $U(T)_{out}$ is obtained, the slope of which, TO, is also stored in said information storing means, and is then used to calculate the off set at a given pressure. The calculated offset will then be deducted from $U(P,T)_{out}$.

The actual pressure is calculated as $$P = (U(P,T)_{out} - TO*U(T)_{out})/K_{37}$$

Other compensation parameters and system parameters may be stored in said storing means, e.g. information regarding inherent imbalance of the bridge.

When an absolute pressure sensor is utilized, variations in ambient pressure will be accounted for by means of a barometer provided inside the control unit.

Second Embodiment (Passive Calibration)

Figure 5:
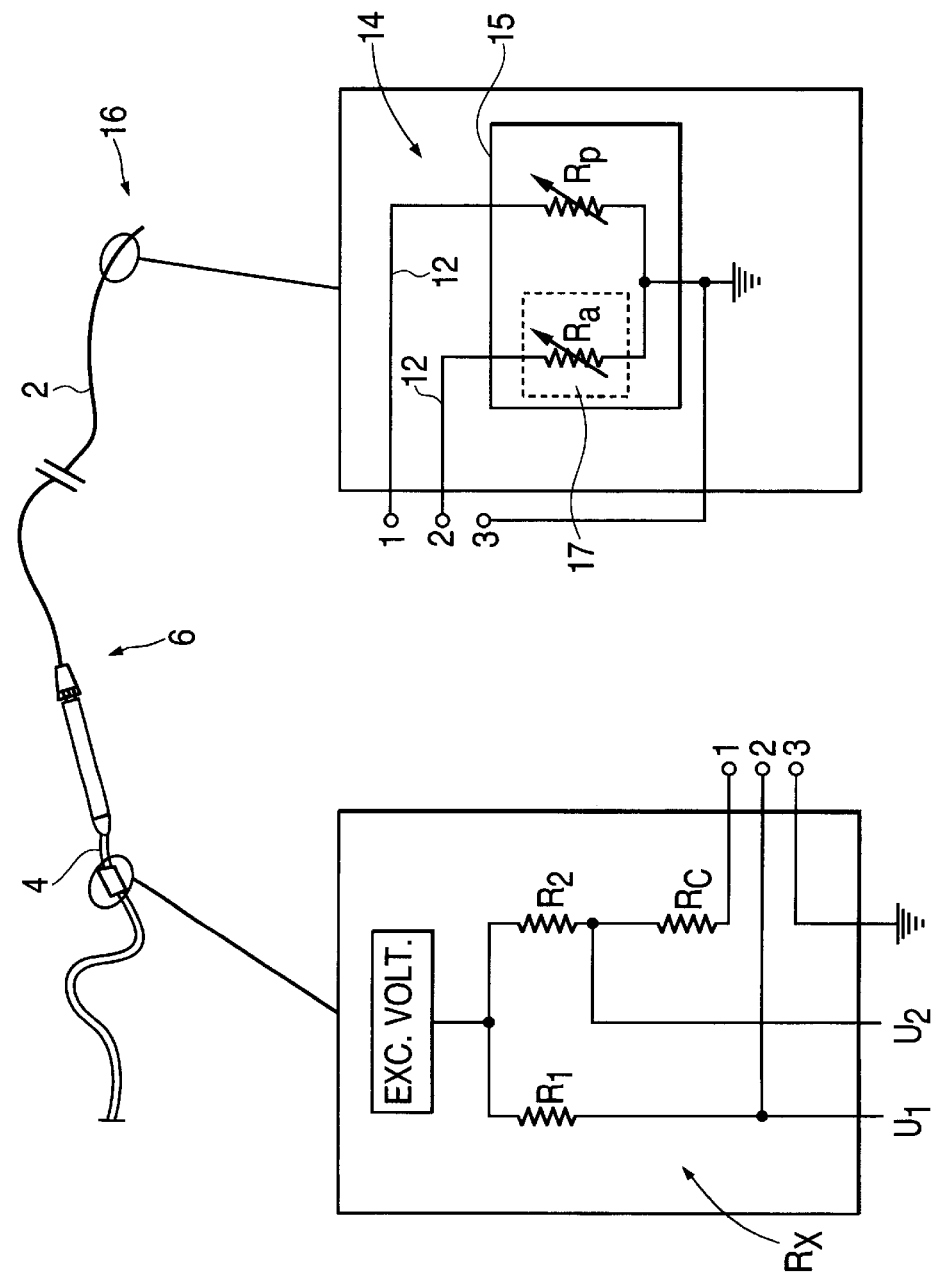
FIG. 5 shows a second embodiment comprising an electrical circuit with a net of resistors for calibration of the sensor.

With reference to FIG. 5, another way of calibrating the sensor will now be described, namely what we refer to as a "passive" temperature calibration. By "passive" we mean that each circuit has been set at manufacture by trimming the resistors to fixed resistance values. This is in contrast to the "active" calibration discussed above, where the temperature dependence characteristics are determined and stored in a PROM, and each measurement signal is temperature compensated at the time of measurement.

The passive calibration balances out the difference in temperature sensitivity of the two resistors on the sensor chip. Therefore the output signal from the measurement circuit can be used as a direct pressure indicative signal.

The resistors on the sensor are labeled as above, $R_a$ for the active (pressure sensitive) and $R_p$ for the passive resistor.

As shown in FIG. 5 the active resistor $R_a$ and the passive resistor $R_p$ are provided on the sensor chip 15, at least $R_a$ being mounted on a membrane 17. $R_p$ is preferably mounted adjacent $R_a$ but on the silicon substrate and not on the membrane in order to eliminate the influence of pressure on the resistance of $R_p$. One end of both resistors are connected to a common terminal at the same electric potential, namely ground. The other ends of $R_a$ and $R_p$ are connected to electrical leads 12, disposed inside the guide wire 2, and ending in a proximal end of said guide wire, forming a male part of a connector device 6. The actual passive calibration circuit is provided on an interface cable 4, i.e. a cable of larger dimensions, interfacing with external power supplies, calculation means such as computers, monitors etc.

The passive calibration circuit comprises three resistors $R_1$, $R_2$ and $R_c$. The resistors $R_a$, $R_p$, $R_1$ and $R_2$ form a Wheatstone bridge, and $R_a$ and $R_p$ are coupled into the two branches respectively of said Wheatstone bridge, whereby $R_1$ and $R_2$ are connected in series to $R_a$ and $R_p$ respectively, whereby the other ends of $R_a$ and $R_p$ are connected to common ground. $R_1$ and $R_2$ are connected to a common excitation voltage source. For brevity the term resistor net denoted $R_x$ is used.

In order to balance out the difference in temperature dependence between $R_a$ and $R_p$, said additional resistor $R_c$ is connected in series in the branch of the bridge having the largest TCR value. TCR (Temperature Coefficient of Resistance) is defined as $$-TCR=-(R_{T2}-R_{T1})/(R_{T1}*(T_2-T_1))$$

wherein T2 represents an elevated temperature, e.g. 40° C., and T1 represents ambient temperature, e.g. 20° C.

Two voltages are of interest, namely $U_1$ existing at a point between $R_a$ and $R_1$, and $U_2$ existing at a point between $R_2$ and $R_c$. Reference is ground potential.

By this compensation the output $U_1-U_2$ will be directly representative of the pressure, and no calculation will be needed to obtain a correct pressure.

A calculation of the value of $R_c$ will be given below as an example.

EXAMPLE

Let us assume that $R_a$=2500 ohm, and has a temperature coefficient (TCR) of 470 ppm/°C., and that $R_p$=2300 ohm, and TCR=500 ppm/°C.

In this case $TCR_p$ should be decreased to the value of $TCR_a$. The following equation (1) can be used to find the value of $R_c$:

$$TC(R_p)_{comp}=TC(R_a)=[(R_{p,T2}+R_c)-(R_{p,T1}+R_c)]/(R_{p,T1}+R_c) \quad (1)$$

which gives $$(TCR_p-TCR_a)/TCR_a*R_p=R_{comp} \quad (2)$$

and inserting the assumed values $$R_{comp}=((500-470)/470))*2300=146.8 \text{ ohm} \quad (3)$$

The bridge is zeroed for atmospheric pressure and 20°C. The values of $R_1$ and $R_2$ are obtained approximately from equation (4):

$$(R_a/R_1)=(R_p+R_c)/(R_2) \quad (4)$$

In practice so called laser trimming, which is a well known technique for balancing resistor nets, may be employed to set $R_c$ to a correct value. As shown in FIG. 5 the resistor $R_c$ is connected in series with $R_p$. However it could happen that the imbalance in the bridge requires that $R_c$ be connected in series with $R_a$. Therefore, in the actual trimming set up, there will be two variable resistors connected in series with $R_a$ and $R_p$ respectively. The trimming procedure is then an iterative procedure where the result of an incremental trimming is fed back and the trimming is adjusted until a balanced bridge is obtained. Therefore, in practice the bridge shown in FIG. 5 is an equivalent representation of an actual bridge.

Other methods of trimming may also be employed, and it is within the ability of the skilled man to find suitable methods. For example is is equally well possible to connect $R_c$ in parallel.

The basic principle of the invention of providing a guide wire assembly in two disconnectable parts, is of course applicable to other measurement types than pressure measurements, e.g. flow measurements, temperature measurements, pH measurements etc. The thing of importance is that the measurement bridge is split/divided in two parts, one part sensitive to the parameter to be measured, and another part non-sensitive to said parameter.

The device according to the invention comprising a guide wire provided with a pressure sensor, is particularly usable for performing pressure measurements in coronary vessels, and for allowing balloon dilation therein by means of a balloon catheter, without the need of removing neither said balloon catheter nor said guide wire and pressure sensor.

To this end a guide catheter is inserted in the arterial vessel and secured therein as a first step. Then, a guide wire having a pressure sensor mounted at its distal end, and a connector at its proximal end is provided. The guide wire is passed inside said guide catheter to a desired measurement location. The guide wire is thus located at a desired measurement location in a coronary vessel.

Then the guide wire is connected to suitable external means for processing pressure signals from said sensor. A pressure measurement is performed if desired. The guide wire is disconnected from said external means, and a balloon catheter is passed onto said guide wire, and located at a desired point for dilatation. The guide wire is again connected to said external means. Dilatation is performed and again a pressure measurement is performed if desired for control purposes.

The invention being thus described, it will be obvious that the same way be varied in many ways. Such variations are not to be regarded as a departure from the spirit and scope of the invention, and all such modifications as would be obvious to one skilled in the art are intended to be included within the scope of the following claims.

What is claimed is:

1. A guide wire assembly, comprising
 a guide wire (2) having a distal end portion (16) and a proximal end, wherein a measuring device (14) is mounted in the distal end portion (16) of said guide wire (2);
 an interface cable (4) having a first end connectable to a control unit (8), and having a second end connectable (6) to the proximal end of said guide wire (2); and information storing means (20; 22; $R_x$) provided on said interface cable (4) and containing calibration-/temperature compensation data, uniquely characteristic of said measuring device (14), said data and an uncompensated output from said measuring device forming the input for calculation of a correct measurement value.

2. The assembly of claim 1 wherein said information storing means is an EPROM (20), containing a calibration curve for said measuring device (14).

3. The assembly of claim 1 wherein said information storing means is a resistor net ($R_a$, $R_p$, $R_1$, $R_2$, $R_c$) comprising a compensation resistor ($R_c$).

4. The assembly of claim 3, wherein said resistor net comprises five resistors ($R_a$, $R_p$, $R_1$, $R_2$, $R_c$), said resistors ($R_a$, $R_p$, $R_1$, $R_2$) forming a Wheatstone bridge, wherein resistor ($R_a$) and resistor ($R_p$) are coupled into the two branches respectively of said Wheatstone bridge, whereby ($R_1$) and ($R_2$) are connected in series to ($R_a$) and ($R_p$) respectively, whereby the other ends of ($R_a$) and ($R_p$) are connected to common ground, and wherein ($R_1$) and ($R_2$) are connected to a common excitation voltage source, and wherein ($R_c$) is connected between ($R_2$) and ($R_p$).

5. The assembly of claim 2, comprising a double Wheatstone bridge, comprising a sensor having an active (pressure dependent resistor) ($R_a$), and a passive (pressure independent element) resistor ($R_p$) mounted in the vicinity of ($R_a$) a first end of both ($R_a$) and ($R_p$) being connected to common ground, and four additional resistors ($R_{1-4}$) being fixed resistors, and located external of said sensor, preferably in an external control unit or on said interface cable, a second end of ($R_a$) being connected via a suitable lead to a first end of one fixed resistor ($R_1$) the second end of ($R_1$) being connected to an excitation voltage source, and a second end of ($R_p$) being connected via a suitable lead to a first end of another fixed resistor ($R_2$), the second end of ($R_2$) being connected to the same excitation voltage source as ($R_1$) said fixed resistors ($R_3$) and ($R_4$) being connected in series to said common ground, and ($R_3$) at the other end being connected to the same excitation voltage as ($R_1$) and ($R_2$).

6. The assembly of claim 1 wherein said information storing means is a bar code (22) provided on a label on said interface cable (4).

7. A guide wire assembly, comprising a guide wire (2) having a distal end portion (16) and a proximal end, wherein a measuring device (14) is mounted in the distal end portion of said guide wire;

an interface cable (4) having a first end connectable to a control unit (8), and having a second end connectable (6) to the proximal end of said guide wire (2) by means of a suitable connector (6); and a Wheatsone bridge comprising two half bridges, one half bridge located on said measuring device (14), the other located on a proximal side of said connector (6).

8. A guide wire assembly for pressure measurements, comprising a guide wire (2) having a distal end portion (16) and a proximal end;

a pressure sensitive element (14) mounted in the distal end portion (16) of said guide wire (2);

an interface cable (4) having a first end connectable to a control unit (8), and having a second end connectable to a proximal end of said guide wire, by means of a connector (6) comprising mating male and female parts, said male part being provided on said guide wire, said female part being provided on said interface cable;

an electrical signal generating circuit comprising a pressure dependent part provided on said guide wire, and a pressure independent part provided on the proximal side of said connector, said pressure sensitive element forming part of said electrical signal generating circuit;

information storing means provided on said interface cable and containing calibration-/temperature compensation data, uniquely characteristic of said sensor element, said data and the uncompensated output from said electrical signal generating circuit means forming the input for calculation of a pressure value.

9. A system for pressure measurements and coronary vessel dilatation, comprising a guide wire (2) having a distal end portion (16) and a proximal end, wherein a pressure measuring device (14) is mounted in the distal end portion (16) of said guide wire (2);

an interface cable (4) having a first end connectable to a control unit (8), and having a second end connectable (6) to the proximal end of said guide wire (2);

information storing means (20; 22; $R_x$) provided on said interface cable (4) and containing calibration-/temperature compensation data, uniquely characteristic of said measuring device (14), said data and an uncompensated output from said measuring device forming the input for calculation of a correct measurement value;

a guide catheter for insertion in the arterial vessels and for guiding said guide wire to its desired location;

a balloon catheter for dilatation adapted to be passed over said guide wire and located at a desired location in said vessel.

10. A guide wire assembly, comprising:

a guide wire having a distal end and a proximal end, a sensor being mounted near the distal end of said guide wire;

a cable having an end connectable to the proximal end of said guide wire; and an electronic device provided on said cable for compensating said sensor.

11. A guide wire assembly as set forth in claim 10, wherein the sensor is a pressure sensor.

12. A guide wire assembly as set forth in claim 10, further comprising a connector between the guide wire and the cable.

13. A guide wire assembly as set forth in claim 10, wherein the electronic device stores compensation data specific to the sensor.

14. A guide wire assembly as set forth in claim 10, wherein the electronic device stores temperature compensation data specific to the sensor.

15. A guide wire assembly as set forth in claim 10, wherein the electronic device includes an EPROM.

16. A guide wire assembly as set forth in claim 10, wherein the electronic device stores pressure compensation data specific to the sensor.

17. A guide wire assembly as set forth in claim 10, wherein the sensor is a flow sensor.

18. A guide wire assembly as set forth in claim 10, wherein the sensor is a temperature sensor.

19. A guide wire assembly as set forth in claim 10, wherein the sensor is a pH sensor.

20. A guide wire assembly as set forth in claim 10, wherein the electronic device includes a resistor net.

21. A guide wire assembly as set forth in claim 10, wherein the electronic device includes a memory.

* * * * *